US006333419B1

(12) United States Patent
Gabetta et al.

(10) Patent No.: US 6,333,419 B1
(45) Date of Patent: Dec. 25, 2001

(54) CHROMATOGRAPHIC SEPARATION METHOD OF PACLITAXEL AND CEPHALOMANNIN

(75) Inventors: Bruno Gabetta; Gianfranco Zini, both of Milan (IT)

(73) Assignee: Indena SpA, Milan (IT)

( * ) Notice: Subject to any disclaimer, the term of this patent is extended or adjusted under 35 U.S.C. 154(b) by 0 days.

(21) Appl. No.: 09/724,504

(22) Filed: Nov. 28, 2000

(51) Int. Cl.$^7$ .................................................. C07D 305/14
(52) U.S. Cl. ............................................. 549/510; 549/511
(58) Field of Search ...................................... 549/510, 511

(56) References Cited

U.S. PATENT DOCUMENTS

| | | | |
|---|---|---|---|
| 5,618,538 | 4/1997 | ElSohly et al. | 424/195.1 |
| 5,670,673 | 9/1997 | Rao | 549/510 |
| 5,856,532 | 1/1999 | Chattopadhyay et al. | 549/510 |
| 6,002,025 | 12/1999 | Page et al. | 549/510 |

OTHER PUBLICATIONS

J.H. Cardellina, "HPLC Separation of Taxol and Cephalomannine", Journal of Liquid Chromatography, 14,659–665, 1991.

S. Richheimer et al., Anal. Chem., "High–performance liquid chromatographic assay of taxol", 64, pp 2323–2326, 1992.

Wickremesinhe et al., "Methodology for the identification and purification of taxol and cephalomannine from taxus callus cultures", Journal of Liquid Chromatography, 16(15), 3263–3274, 1993.

Witherup et al., High performance liquid chromatographic separation of taxol and related compounds from taxus brevifolia:, Journal of Liquid Chromatography, 12(11), 2117–2132, 1989.

Witherup et al., "Taxus Spp. needles contain amounts of taxol comparable to the bark of taxus brevifolia: analysis and isolation", Journal of Natural Products, vol. 53, No. 5, 1249–1255, 1990.

Kelsey, et al., "Taxol and cephalomannine concentrations in the foliage and bark of shade–grown and sun–exposed taxus brevifolia trees", Journal of Natural Products, vol. 55, No. 7, 912–917, 1992.

Wheeler et al., "Effects of genetic epigenetic, and environmental factors on taxol content in taxus brevifolia and related species", Journal of Natural Products, vol. 55, No. 4, 432–440, 1992.

Kingston et al., "Modified taxols, 7. A method for the separation of taxol and cephalomannine", Journal of Natural Products, vol. 55, No. 2, 259–261, 1992.

Beckvermit et al., "An improved method for separating paclitaxel and cephalomannine using ozone and girard reagents", J. Org. Chem., 61, 9038–9040, 1996.

Rimoldi et al., "An improved method for the separation of paclitaxel and cephalomannine", Journal of Natural Products, 59, 167–168, 1996.

Blechert et al., "Mise en evidence de nouveaux analogues du taxol extraits de taxus baccata", Journal of Natural Products, vol. 47, No. 1, 131–137, 1984.

Chmurny et al., "H– and C–NMR assignment for taxol, 7–epi–taxol, and cephalomannine", Journal of Natural Products, vol. 55, 414–423, 1992.

Falzone et al., "Characterization of taxol in methylene chloride by NMR spectroscopy", 33(9), pp. 1169–1172, 1992.

M.C. Wani et al., "Plant Antitumor Agents VI. The Isolation and Structure of Taxol, A Novel Antileukemic and Antitumor Agent From *Taxus Brevifolia*," J. Amer. Chem. Soc., 93, (9), 2325–2327, 1971.

*Primary Examiner*—Ba K. Trinh
(74) *Attorney, Agent, or Firm*—Pennie & Edmonds LLP

(57) ABSTRACT

A method for separating paclitaxel from cephalomannin and other related compounds by obtaining a starting material that contains paclitaxel and cephalomannin; dissolving the starting material in any one of a number of particularly defined solvents such as butyl formate and butyl acetate to form a mixture; subjecting the mixture to column chromatography to obtain an eluted fraction of paclitaxel, an eluted fraction of cephalomannin and a residue; and separately drying the paclitaxel and cephalomannin fractions to obtain separate crystalline forms of paclitaxel and cephalomannin, respectively.

14 Claims, No Drawings

CHROMATOGRAPHIC SEPARATION METHOD OF PACLITAXEL AND CEPHALOMANNIN

FIELD OF THE INVENTION

This invention is directed to the separation of paclitaxel from its analogue cephalomannin starting from extracts of plants of the genus Taxus or their cell cultures. In particular, paclitaxel is separated from cephalomannin through chromatography on direct-phase silica gel columns.

BACKGROUND ART

Paclitaxel, formerly called "Taxol" is an exceptionally promising anticancer agent. It was isolated from the bark of *Taxus brevifolia* by Wani et al. in 1971 (J. Am. Chem. Soc. 93, 2325, 1971) and its structure was defined using chemical methods and X-ray crystallographic analysis.

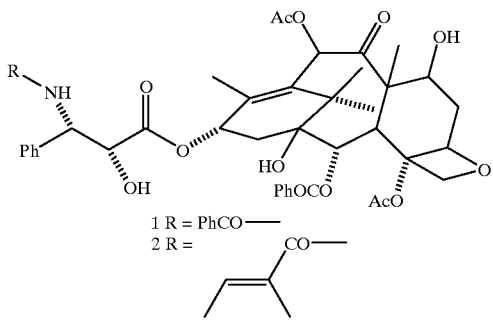

1 R = PhCO—
2 R = /C(CH₃)=CH(CH₃)CO—

Paclitaxel has been approved by the Food and Drug Adminstration for the treatment of breast and ovarian cancer and is currently in clinical trials for the treatment of lung and colon cancers (for example, see W. P. McGuire and E. K. Rowinsky, Paclitaxel in Cancer Treatment, M. Dekker, New York 1995, pages 1 to 337).

A primary natural source for paclitaxel is the bark of the Pacific Yew tree, *Taxus brevifolia*. It has also been found that paclitaxel is present in the epigeal parts and the roots of other yew species, including the European yew (*Taxus baccata*), Asian yews (*Taxus wallichiana* and *Taxus chinensis*), and yew trees cultivated for ornamental purposes (for example, *Taxus media*).

The method of isolation of paclitaxel from any natural resource is complex and expensive, partly because of the relatively low concentrations in vegetable materials but also because of the presence of one of its congeners, cephalomannin. The contents of and ratios between paclitaxel and cephalomannin vary in vegetable materials depending on the species and the part of the plant in question. In general, it has been found that the content of paclitaxel and cephalomannin ranges from 0.001% to 0.08% and 0.001% to 0.22% respectively (K. M. Witherup et al., J. Nat. Prod., 53,1249, 1990; R. G. Kelsey et., J. Nat. Prod., 55, 912, 1992; N. C. Wheeler et al., J. Nat. Prod., 55,432, 1992). In particular, the *Taxus media* species which, being renewable vegetable material, is the most commonly used raw material for the preparation of paclitaxel, contains on the average the highest concentration of cephalomannin in comparison with the other species.

Even the paclitaxel production techniques based on yew cell cultures, which have recently been given a substantial boost to obviate the conventional extraction of expensive vegetable material, yield a relevant quantity of cephalomannin in addition to paclitaxel.

The only structural difference between paclitaxel and cephalomannin involves the side chain portion of the compound, thus giving rise to similar chemical properties. The two compounds, therefore, possess very similar chromatographic properties and clean separation of these related compounds is difficult. A number of chromatographic methods, mainly based on the use of inverted-phase chromatography or expensive bonded-phase columns, have been proposed (J. H. Cardellina, J. Liq. Chromatogr., 12, 2117, 1989), but these cannot be easily adapted to a large commercial scale operation. For this reason, the availability of methods allowing the separation of paclitaxel and cephalomannin remains a topic of great practical importance.

In the past, paclitaxel and cephalomannin separation methods, based on the different reactivity of the two compounds to oxidants, were proposed. It was found that the double olefin bond existing in the tiglic residue of cephalomannin could be oxidized by reaction with osmium tetroxide (D. G. I. Kingston et al., J. Nat. Prod., 55, 259, 1992) or ozone (J. T. Beckvermit et al., J. Org. Chem., 61, 9038, 1996), while paclitaxel did not undergo any chemical transformation during oxidation reactions. Another approach considered the treatment of mixtures of paclitaxel and cephalomannin with bromine (J. M. Rimoldi et al., J. Nat. Prod., 59, 167, 1996). Treatment with bromine, performed under controlled temperature and time reaction conditions, causes the formation of dibromocephalomannin, while paclitaxel is not affected by this chemical reagent. These methods, however, have a drawback in their use of such toxic reagents as osmium tetroxide and, in any case, result in the destruction or transformation of cephalomannin into its derivatives, from which cephalomannin can be regenerated only through difficult synthetic processes. There is still a need, therefore, for in inexpensive, simple, safe and effective separation of cephalomannin from paclitaxel. Accordingly, the primary objective of this invention is to provide a simple method to separate paclitaxel and cephalomannin from their mixtures or yew extracts.

SUMMARY OF THE INVENTION

The present invention provides a method for separating paclitaxel from cephalomannin and other related compounds. In particular, this method comprises obtaining a starting material that contains paclitaxel and cephalomannin; dissolving the starting material in any one of a number of particularly defined solvents to form a mixture; subjecting the mixture to column chromatography to obtain an eluted fraction of paclitaxel, an eluted fraction of cephalomannin and a residue; and separately drying the paclitaxel and cephalomannin fractions to obtain separate crystalline forms of paclitaxel and cephalomannin, respectively. The solvent is preferably butyl formate or butyl or benzyl acetate.

DETAILED DESCRIPTION OF THE INVENTION

Surprisingly, it was found that highly pure palitaxel and cephalomannin could be obtained with great yields by chromatographic separation on one direct phase silica gel column using one solvent as the elutant. Preferably, this solvent has the following general formula:

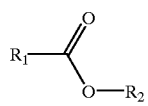

where $R_1$ is hydrogen or methyl and $R_2$ preferably contains four carbon atoms, that is, it may be n-butyl, isobutyl, sec-butyl or t-butyl. These solvents are not frequently used in routine chromatographic purification on column, but provide surprisingly good practical results in the specific case of the paclitaxel-cephalomannin separation.

The starting material of this invention may be a mixture of cephalomannin and paclitaxel alone in any ratio or extract of fresh or dry Taxus roots, leaves, branches, seeds or their mixtures. The method of this invention may also involve an extract obtained from a cell culture. These starting materials are generally known to one of ordinary skill in the art so that they do not need to be further mentioned herein.

The extract in question may be a raw or a purified extract—the latter having been treated with conventional solvents and subjected to preliminary chromatographic purification. Again, these techniques are well know to the skilled artisan so that no further mention need be made herein. The starting material may be in the form of a solid, a syrup or a semisolid gummy material, depending on the experimental conditions used for its preparation. The material may simply be subjected to column chromatography following its dissolution in one of the solvents described herein.

The chromatographic purification of the invention utilizes a simple, direct-phase silica gel in a quantity of about 50 to 100 parts in weight of the starting material, depending on its composition.

Column chromatography with the solvents of the invention is fast, does not require high pressures and is performed in normal gravity conditions.

Table 1 shows the behavior of cephalomannin and paclitaxel in the thin-layer chromatographic analysis using silica gel plates and a series of the solvents of the invention which allow a satisfactory separation of the two compounds.

TABLE 1

Rf values of paclitaxel and cephalomannin on silica gel plates

| Solvent | $R_1$ | $R_2$ | Paclitaxel | Cephalomannin |
|---|---|---|---|---|
| n-Butyl formate | H | n-$C_4H_9$ | 0.17 | 0.12 |
| i-Butyl formate | H | i-$C_4H_9$ | 0.20 | 0.15 |
| t-Butyl formate | H | t-$C_4H_9$ | 0.20 | 0.13 |
| n-Butyl formate | $CH_3$ | n-$C_4H_9$ | 0.36 | 0.28 |
| s-Butyl formate | $CH_3$ | s-$C_4H_9$ | 0.35 | 0.24 |
| i-Butyl acetate | $CH_3$ | i-$C_4H_9$ | 0.31 | 0.19 |
| t-Butyl acetate | $CH_3$ | t-$C_4H_9$ | 0.19 | 0.09 |
| Benzyl acetate | $CH_3$ | $PhCH_2$ | 0.28 | 0.16 |

The use of the solvents described in this invention to isolate paclitaxel and cephalomannin through chromatography on a direct-phase silica gel column offers a number of advantages.

First, column chromatography yields virtually cephalomannin-free paclitaxel and, conversely, almost paclitaxel-free cephalomannin. Second, the use of direct-phase silica gel offers considerable economic advantages over the use of the inverted-phase silica gels described in the above literature, and thirdly, the use of one solvent for the elution of the column allows its rapid recycling without resort to fractional distillation in operations connected to industrial, continuous-process preparations. Any other constituents present in the starting material together with paclitaxel and cephalomannin are eliminated through chromatographic purification.

The eluted fractions are vacuum-evaporated to dryness, and the residues are crystallized by a suitable solvent to obtain paclitaxel and cephalomannin in the desired crystalline form.

The method described in this invention, therefore, provides a simple solution for the preparation of considerable quantities of cephalomannin-free paclitaxel, by increasing the yield of the amounts obtained and promoting a cheaper production process of this antitumoral drug.

EXAMPLES

The following examples illustrate, but do not limit, this invention.

Example 1

Isolation of Paclitaxel from *Taxus media* Extract Containing Cephalomannin 290 g extract, prepared from 620 kg *Taxus media* (whole plant) according to the process described by V. Senilh et al. (J. Nat. Prod. 47, 131, 1984), is found to contain 183 g paclitaxel and 81 g cephalomannin by means of HPLC analysis. The extract is dissolved in 3.5 L t-butyl acetate and loaded onto a column containing 60kg silica gel. A total 1,200 L t-butyl is eluted. A 400 L fraction containing paclitaxel and less than 3% cephalomannin and another 200 L fraction containing cephalomannin and less than 3% paclitaxel are obtained following elution of 350 L solvent. The two fractions are vacuum-concentrated to dryness separately and the residues are crystallized by hexane-acetone. The 154 g paclitaxel and 70 g cephalomannin thus obtained have HPLC purity over 99%, and their physicochemical and spectroscopic values agree with the information provided by literature (G. N. Chmurny et al., J. Nat. Prod. 55, 414, 1992; C. J. Falzone et al., Tetrahedron Letters, 33, 1169, 1992; V. Senilh et al. J. Nat. Prod. 47, 131, 1984).

Example 2

Isolation of Paclitaxel and Cephalomannin from a Mixture Containing Both

A mixture containing 70 g paclitaxel and 30 g cephalomannin is dissolved in 1.5 L t-butyl formate and loaded onto a column containing 10 kg silica gel suspended in the same solvent. The column is eluted with t-butyl formate, and the fractions are joined after HPLC/TLC analysis. The fractions containing paclitaxel and cephalomannin are concentrated to dryness separately and the residues crystallized by acetone and heptane in suitable rations to yield paclitaxel and cephalomannin having a HPLC purity over 99%.

What is claimed is:

1. A method for separating paclitaxel from cephalomannin which comprises:

obtaining a starting material that contains paclitaxel and cephalomannin;

dissolving the starting material in a solvent having the following formula:

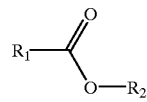

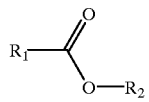

where $R_1$ is hydrogen or methyl and $R_2$ is an alkyl or arylalkyl group containing four to seven carbon atoms, to form a mixture;

subjecting the mixture to column chromatography to obtain an eluted fraction of paclitaxel, an eluted fraction of cephalomannin and a residue; and separately drying the paclitaxel and cephalomannin fractions to obtain separate crystalline forms of paclitaxel and cephalomannin, respectively.

2. The method of claim 1, wherein said starting material contains any ratio of cephalomannin and paclitaxel.

3. The method of claim 1, wherein said starting material is an extract of fresh or dry Taxus roots, leaves, branches, seeds, or their mixtures.

4. The method of claim 1, wherein said starting material is an extract obtained from a cell culture of Taxus material.

5. The method of claim 1, wherein said starting material is in the form of a solid, a syrup, or a semisolid gummy material.

6. The method of claim 1, wherein the solvent structure includes $R_1$ as hydrogen or methyl and $R_2$ as n-butyl, isobutyl, sec-butyl or t-butyl.

7. A method for separating paclitaxel from cephalomannin which comprises:

obtaining a starting material that contains paclitaxel and cephalomannin;

dissolving the starting material in a solvent having the following formula:

where $R_1$ is hydrogen or methyl and $R_2$ is an alkyl or arylalkyl group containing four to seven carbon atoms, to form a mixture;

subjecting the mixture to column chromatography utilizing a direct-phase silica gel column with using a single solvent of the formula given above as an elutant to obtain an eluted fraction of paclitaxel, an eluted fraction of cephalomannin and a residue; and separately drying the paclitaxel and cephalomannin fractions to obtain separate crystalline forms of paclitaxel and cephalomannin, respectively.

8. The method of claim 7, wherein the solvent formula includes $R_1$ as hydrogen or methyl and $R_2$ as n-butyl, isobutyl, sec-butyl or t-butyl.

9. The method of claim 7 wherein the silica gel is used in a quantity of about 50 to 100 parts in weight of the starting material.

10. The method of claim 7, wherein said starting material contains any ratio of cephalomannin and paclitaxel.

11. The method of claim 7, wherein said starting material is an extract of fresh or dry Taxus roots, leaves, branches, seeds, or their mixtures.

12. The method of claim 7, wherein said starting material is an extract obtained from a cell culture of Taxus material.

13. The method of claim 7, wherein said starting material is in the form of a solid, a syrup, or a semisolid gummy material.

14. The method of claim 7, wherein the solvent formula includes $R_1$ as hydrogen or methyl and $R_2$ as n-butyl, isobutyl, sec-butyl or t-butyl.

\* \* \* \* \*

UNITED STATES PATENT AND TRADEMARK OFFICE
CERTIFICATE OF CORRECTION

PATENT NO. : 6,333,419 B1
DATED : December 25, 2001
INVENTOR(S) : Bruno Gabetta and Gianfranco Zini It is certified that error appears in the above-identified patent and that said Letters Patent is hereby corrected as shown below:

<u>Column 2,</u>
Lines 10-11, replace "(J. H. Cardellina, J. Liq. Chromatogr., 12, 2117, 1989)" with -- (J. H. Cardellina, J. Liq. Chromatogr., <u>14</u>, 659, 1991; S.L. Richheimer et al., Anal. Chem. <u>64</u> , 2323, 1992; E.R.M. Wickremesinhe et al., J. Liq. Chromatogr., <u>16</u>, 3263, 1993; K.M. Witherup et al., J. Liq. Chromatogr., <u>12</u>, 2117, 1989) --.

Signed and Sealed this

Twentieth Day of August, 2002

Attest:

Attesting Officer

JAMES E. ROGAN
Director of the United States Patent and Trademark Office